(12) United States Patent
Pitzen et al.

(10) Patent No.: US 6,842,646 B2
(45) Date of Patent: Jan. 11, 2005

(54) APPARATUS FOR THE ELECTRICAL STIMULATION OF HUMAN TISSUE

(75) Inventors: Sylvester A. Pitzen, Phoenix, AZ (US); Stephen M. Monnig, Glendale, AZ (US)

(73) Assignee: Sono-Therapy Institute, Inc., Phoenix, AZ (US)

( * ) Notice: Subject to any disclaimer, the term of this patent is extended or adjusted under 35 U.S.C. 154(b) by 92 days.

(21) Appl. No.: 10/295,680

(22) Filed: Nov. 15, 2002

(65) Prior Publication Data

US 2004/0098066 A1 May 20, 2004

(51) Int. Cl.[7] .................................................. A61N 1/08
(52) U.S. Cl. .............................. 607/50; 607/2; 607/68; 607/73
(58) Field of Search .......................... 607/2, 50, 68–70, 607/72–73, 115, 139

(56) References Cited

U.S. PATENT DOCUMENTS

| | | | | |
|---|---|---|---|---|
| 3,872,859 A | | 3/1975 | Pitzen et al. ................... 601/15 |
| 5,018,524 A | * | 5/1991 | Gu et al. ...................... 607/68 |
| 5,107,835 A | * | 4/1992 | Thomas ....................... 607/46 |
| 5,131,389 A | * | 7/1992 | Giordani ...................... 607/47 |
| 5,484,387 A | | 1/1996 | Pitzen ......................... 601/15 |
| 6,535,767 B1 | * | 3/2003 | Kronberg ..................... 607/72 |

* cited by examiner

*Primary Examiner*—Carl Layno
*Assistant Examiner*—B. Webb
(74) *Attorney, Agent, or Firm*—Jordan M. Meschkow; Lowell W. Gresham; Meschkow & Gresham, P.L.C.

(57) ABSTRACT

An apparatus (22) for applying a therapeutic signal (31) to the scalp (32) of a subject (20) includes a first electrode (26) for massaging the scalp (32) and second electrode (30) in contact with the subject (20) and located remote from the first electrode (26). The therapeutic signal (31), passing between the first and second electrodes (26, 30) through the scalp (32), serves to loosen connective tissue and improve blood circulation in the scalp. The apparatus (22) includes digital waveform generators (54) for generating harmonically non-related resultant signals (96). The resultant signals (96) are combined to form the therapeutic signal (31) exhibiting a pseudorandom signal characteristic.

19 Claims, 6 Drawing Sheets

| CHANNEL | N | HIGH FREQUENCY (HZ) | M | LOW FREQUENCY (HZ) |
|---|---|---|---|---|
| 1 | 3826 | 3920 | 252 | 11.90 |
| 2 | — | — | 442 | 6.79 |
| 3 | 1620 | 9260 | 400 | 7.50 |
| 4 | 1110 | 13,510 | 528 | 5.68 |
| 5 | — | — | — | — |
| 6 | — | — | 2830 | 1.06 |
| 7 | 4424 | 3390 | 360 | 8.33 |
| 8 | — | — | 408 | 7.35 |
| 9 | 1800 | 8330 | 736 | 4.08 |
| 10 | 1350 | 11,110 | 690 | 4.35 |
| 11 | 1006 | 14,910 | 1172 | 2.56 |
| 12 | 974 | 15,400 | 3264 | 0.92 |

FIG. 5

APPARATUS FOR THE ELECTRICAL STIMULATION OF HUMAN TISSUE

RELATED PATENTS

The present invention is related to:

"Method And Device For Loosening Connective Tissue And Stimulating Blood Circulation," by Sylvester A. Pitzen, U.S. Pat. No. 5,484,387, issued 16 Jan. 1996, and incorporated by reference herein.

TECHNICAL FIELD OF THE INVENTION

The present invention relates to the field of electrical stimulation of human tissue. More specifically, the present invention relates to an apparatus for providing a therapeutic signal to aid in loosening connective tissue and stimulating blood circulation.

BACKGROUND OF THE INVENTION

In an age of great emphasis on youth and beauty, hair loss has become a major concern. Indeed, some sort of baldness (alopecia) affects a significant percentage of the total male population. Some women also experience thinning of the hair as they age, although baldness in women is rare. Male pattern baldness is the most common form of baldness, and begins with hair loss from the vertex and the frontoparietal regions of the scalp, ultimately leaving only a sparse peripheral rim of scalp hair. A hair follicle is a tube-like opening into the epidermis where a hair develops, and a hair root is the part of a hair that is embedded in the hair follicle. In affected areas, the hair follicles produce finer and lighter terminal hairs until terminal hair production ceases.

The cause of male pattern baldness is unknown. However, it is theorized that male pattern baldness may be caused by a combination of factors that include, for example, the vascular composition of the individual, the physical structure of an individual's scalp, aging, and the male characteristic hormone, testosterone. In other words, poor blood circulation in the scalp, non-elasticity of the scalp tissue resulting from increased cross-linkage of connective tissue, loss of skin elasticity due to aging, and testosterone play a role in male pattern baldness. This combination of factors is believed to cause the hair follicles to shorten and cease to produce hair.

In response to the distress of those suffering from male pattern baldness, a multitude of treatments have been devised in an attempt to stop and/or reverse the process of hair loss. These treatments include medications, hair transplants, scalp exercise, low voltage electrical stimulation, and so forth. Although many have claimed to have solved the problem, in whole or in part, there has yet to be found a definitive solution that will truly reverse the process of hair loss.

One technique that has met with limited success is disclosed in U.S. Pat. No. 5,484,387. The '387 patent discloses a method and device for applying low voltage electrical stimulation to the skin layers of the scalp coupled with massage. The device is configured to generate numerous square wave voltage waveforms, each of a different frequency. These are turned on and off at various intervals, to yield a continuously varying signal. The combined use of low voltage electrical stimulation and massage is believed to loosen the skin layers and connective tissue in the scalp. The treatment has resulted in the retardation of hair loss for some, and has resulted in the rejuvenation of hair growth in others.

Unfortunately, there are some problems associated with the device described in U.S. Pat. No. 5,484,387. For example, the device of the '387 patent has a fixed hardware structure. In such a fixed hardware structure, it is not feasible to update the signal characteristics, for example, the frequencies, voltages, waveform shape, and so forth without incurring significant hardware redesign and rebuild.

The rise time (or fall time) of a waveform is the time required to change from one level to another, for example, to rise from ten percent of its peak value to ninety percent of its peak value, and vice versa. It is believed that in the fixed hardware structure described in the '387 patent, the rise time and fall time of the generated square waves is undesirably slow. This results in a less than optimum therapeutic signal and less effective treatment.

It is believed that administration of the treatment is enhanced by a perceived "operator feel." That is, an operator must be trained to experience a physical sense of increased resistance to the massaging action in the region of taut skin and dense connective tissue. When stimulated by electricity, this physical sense of increased resistance is enhanced. It is theorized that the electrical impulse stimulation causes tightening of the connective tissue in those areas where the skin layers are already tight. Accordingly, through the use of electricity, an operator can feel a more noticeable resistance to skin movement in the tight regions. Treatment can then be focused on the tight regions, thereby speeding up the effectiveness of the treatment. Unfortunately, through the use of the device of the '387 patent, this physical sensation is not as frequently experienced as desired, resulting in undesirably lengthy operator training and/or less effective treatments.

Accordingly, what is needed is an improved apparatus capable of generating an optimal therapeutic signal for the electrical stimulation of human tissue.

SUMMARY OF THE INVENTION

Accordingly, it is an advantage of the present invention that a improved apparatus is provided for generating a therapeutic signal for the electrical stimulation of human tissue.

It is another advantage of the present invention that an apparatus is provided in which the therapeutic signal may be readily modified.

Yet another advantage of the present invention is that an apparatus is provided that intensifies "operator feel" to focus and enhance the effectiveness of the treatment.

The above and other advantages of the present invention are carried out in one form by an apparatus for the electrical stimulation of human tissue. The apparatus includes a signal generator for providing a reference signal at a reference frequency. A plurality of digital waveform generators are in communication with the signal generator for producing different resultant signals. Each of the digital waveform generators includes a frequency divider for dividing the reference frequency of the reference signal to produce one of the resultant signals. A combiner is in communication with an output of each of the plurality of digital waveform generators. The combiner combines the resultant signals from each of the digital waveform generators to produce a therapeutic signal. A first electrode is in communication with the combiner, and a second electrode is maintained at a ground potential from which the therapeutic signal from the first electrode is referred. The therapeutic signal has an electrical potential sufficient to stimulate the human tissue.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

FIG. 5 shows a table of frequencies used to produce resultant signals that are combined to form a therapeutic signal;

DETAILED DESCRIPTION OF THE PREFERRED EMBODIMENTS

The primary focus of the present invention is directed to the enhancement of conditions favorable for hair growth. In particular, the present invention serves to loosen connective tissue and improve blood circulation in the scalp. However, the loosening of connective tissue and improved blood circulation have benefits for other physical impairments as well. Injuries or disease affecting body tissue may similarly reduce elasticity of tissue and create blood circulation problems. As such, the treatment discussed herein may alternatively be applied to other areas of the body to improve the condition of connective tissue and blood circulation.

Figure 1:
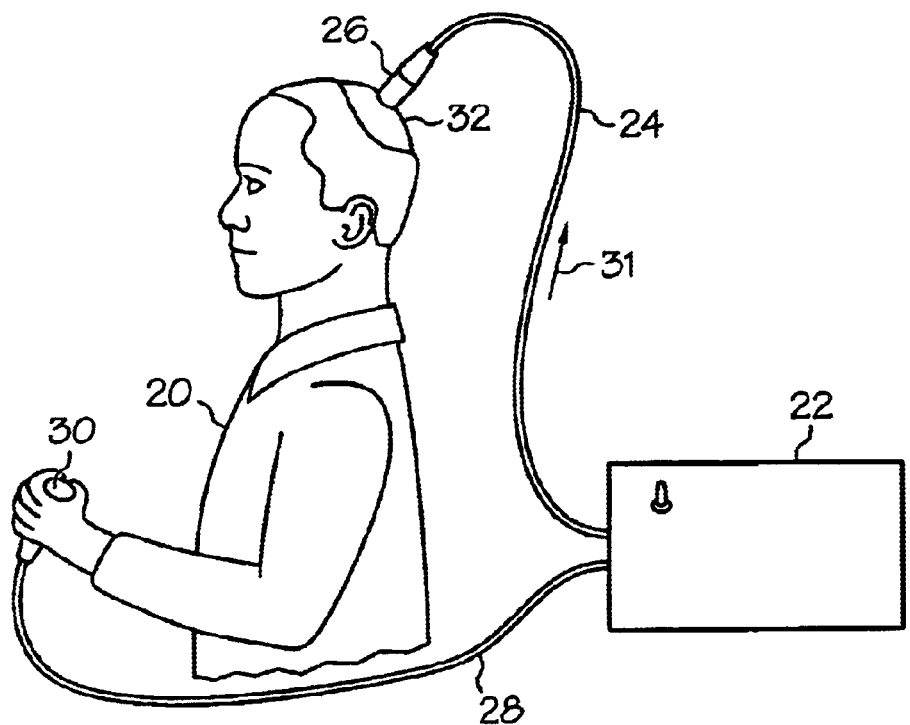
FIG. 1 shows a side view of a subject upon which an apparatus in accordance with the present invention is being utilized.

FIG. 1 shows a side view of a subject 20 upon which an apparatus 22 in accordance with the present invention is being utilized. Apparatus 22 includes a first conductor 24 terminating at a first electrode 26 and a second conductor 28 terminating at a second electrode 30. Second electrode 30 is maintained at a ground potential from which a therapeutic signal, represented by an arrow 31, from first electrode 26 is referred.

Each of first and second electrodes 26 and 30 are fabricated from highly conductive material, such as, gold plating or fine silver, which is at least ninety-nine percent pure silver. Alternatively, or in addition, conductive gel may be used between the subject and the electrode. The highly conductive material and gel enable low resistance between the electrode and subject. First electrode 26 is in contact with the scalp 32 of subject 20, and second electrode 30 is gripped by subject 20. Therapeutic signal 31 passes between first and second electrodes 26 and 30, respectively, via scalp 32, through the body of subject 20.

Figure 2:
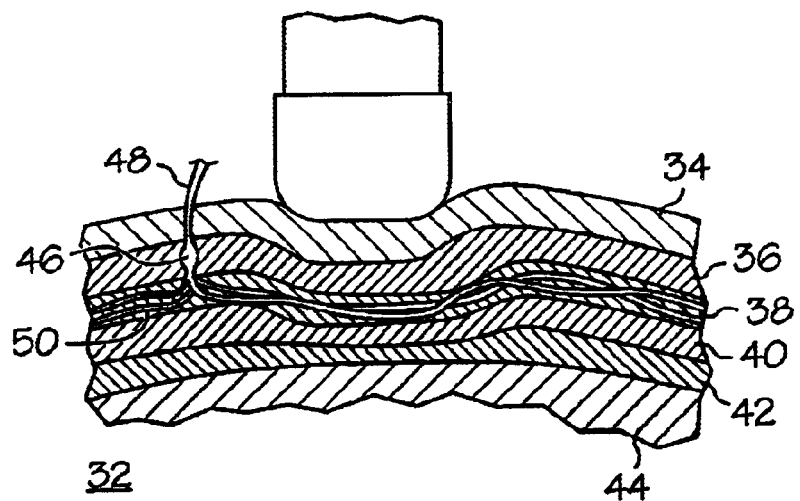
FIG. 2 shows an enlarged cross-section view of the scalp of the subject of FIG. 1 upon which treatment is being applied.

FIG. 2 shows a enlarged cross-section view of a portion of scalp 32 upon which treatment is being applied. In general, scalp 32 includes the epidermis 34, the dermis 36, the adipose tissue layer 38, and the epicranial aponeurosis, or galea 40. Galea 40 is a thin tendinous sheet, tightly attached to dermis 36 and is moveable anteriorly and posteriorly. Loose areolar connective tissue 42 loosely connects galea 40 to the periosteum of the skull bone 44. Connective tissue 42 is an irregularly arranged connective tissue that is generally made up largely of interlacing fibers. Skull bone 44 forms a rigid base upon which scalp 32 rests. Hair follicles 46, of which one is shown, are embedded in scalp 32. A hair 48 extends from hair follicle 46 above scalp 32. Blood vessels 50 provide oxygenation and nourishment to the hair root and hair follicles 46.

When scalp 32 moves freely upon skull 44, scalp 32 is considered herein to be "loose", and the organs within scalp 32 are free to function properly. It is believed that the aging process causes a thickening and tightening of the skin layers, particularly in the underlying galea 40 and connective tissue 42. When galea 40 is greatly thickened and tightened, scalp 32 cannot move freely upon skull 44. Thus, scalp 32 is considered herein to be "tight", and the organs within scalp 32 are prohibited from normal functioning. More specifically, the aging process tends to restrict blood flow through blood vessels 50, which in turn causes a shrinking of hair follicles 46. The shrinking or shortening of hair follicles 46 causes a withdrawal of the hair root and hair follicles 46 from blood vessels 50 to impede nourishment of the hair roots and hair follicles 46. The gradual growth dormancy results in hair loss. Since galea 40 does not thicken and harden consistently throughout its area, a given scalp 32 may have both tight spots and loose spots.

Therapeutic signal 31, produced by apparatus 22 is a low voltage electrical variable impulse signal in the range of, for example −0.250 volt and 1.350 volt. Therapeutic signal 31 has an electrical potential sufficient to stimulate scalp 32. Therapeutic signal 31 penetrates through scalp 32 and particularly through galea 40 and connective tissue 42. Simultaneously, particularly where the operator is able to detect tightness of skin, the total skin thickness, i.e., all the skin layers, is "worked" to loosen the layers. Repeated massage and electrical stimulation acts as nerve stimulation which facilitates a "reawakening" or reversal of the natural nourishment processes in the scalp, which have gradually ceased to function properly on their own.

Figure 3:
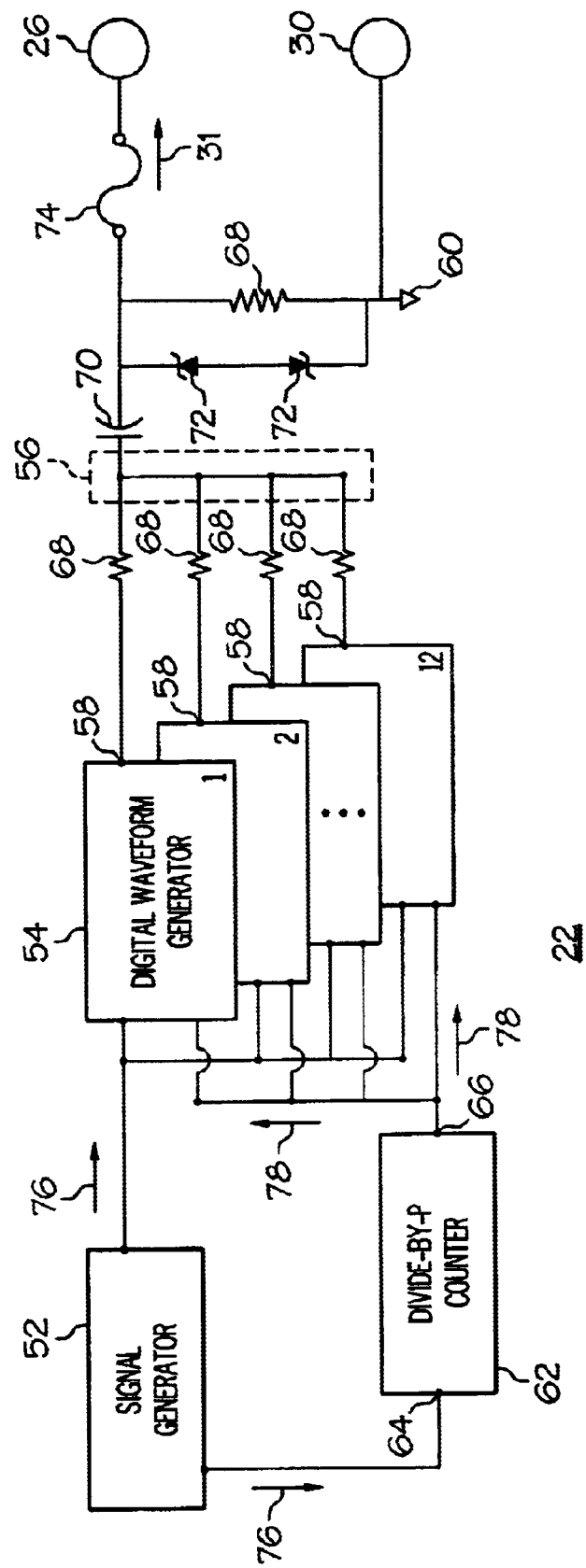
FIG. 3 shows a block diagram of an apparatus of the present invention.

FIG. 3 shows a block diagram of apparatus 22 of the present invention. Apparatus 22 includes a signal generator 52 and a plurality of digital waveform generators 54 in communication with signal generator 52. A combiner, generally denoted by dashed lines 56, is in communication with an output 58 of each of waveform generators 54. First electrode 26 is in electrical communication with combiner 56, and second electrode 30 is maintained at a ground potential 60. Apparatus 22 may be powered by one hundred twenty volt AC household power (not shown) which is subsequently transformed by apparatus 22 into square waves.

Apparatus 22 further includes a divide-by-P counter 62. Divide-by-P counter 62 has a divider input 64 in communication with signal generator 52 and a divider output 66 in communication with each of digital waveform generators 54. Resistors 68, a capacitor 70, diodes 72, and a fuse 74 are configured in accordance with conventional electrical circuit practices for providing signal isolation and safety mechanisms.

In a preferred embodiment, apparatus 22 is a field programmable gate-array (FPGA) design. An FPGA is a specialized microprocessor that contains a large quantity of logic gates which are not interconnected, and whose function is determined by a wiring list that is downloaded to the FPGA. The wiring list determines how the gates are interconnected, and this interconnection is performed dynamically by turning semiconductor switches on or off to enable the different connections.

Programming an FPGA requires a software tool in which the logic functions are defined. An analysis tool then verifies the logic functions and the expected timing of the signals in the device. A layout tool physically maps the logic devices to specific elements on the chip and determines their actual wiring. FPGAs are advantageous over a fixed hardware structure because the function of a piece of hardware can be updated "in the field" by a programmer. The FPGA design enables apparatus 22 to be readily reprogrammed to modify the therapeutic signal while in place, without need for disassembly, replacing components, and so forth. In an exemplary embodiment, the configuration of apparatus 22 is accomplished through the implementation of a Spartan-II Development Kit, manufactured by Insight MEMEC, San Diego, Calif.

In operation, signal generator 52 provides a first reference signal, represented by an arrow 76, to each of digital waveform generators 54 and to divide-by-P counter 62. In an exemplary embodiment, first reference signal 76 may be a 15 MHz clock signal that is input into each of digital waveform generators 54, and into divide-by-P counter 62. Each of digital waveform generators 54 is configured to produce a resultant signal related to first reference signal 76, discussed below.

Divide-by-P counter 62 is a frequency divider that produces a second reference signal, represented by an arrow 78, related to first reference signal 76. In an exemplary embodiment, divide-by-P counter 62 is configured such that "P" is five thousand. Accordingly, when reference signal 76 is 15 MHz, divide-by-P counter 62 produces second reference signal 78 of 3 kHz. Second reference signal 78 of 3 kHz is subsequently provided to each of digital waveform generators 54, as will be discussed in greater detail below. In general, the resultant signal produced by each of digital waveform generators 54 is also related to second reference signal 76, discussed below.

Figure 4:
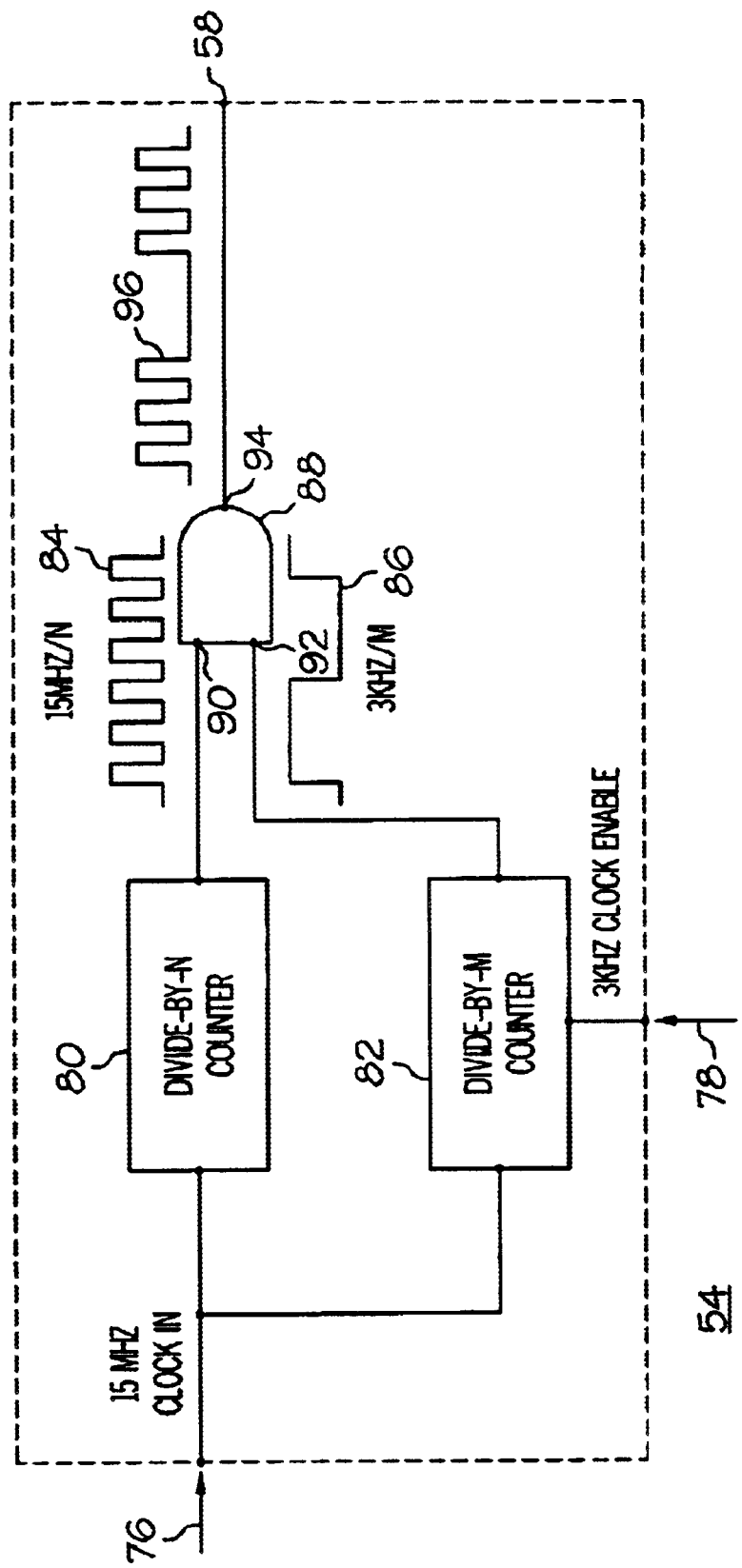
FIG. 4 shows a block diagram of a digital waveform generator of the apparatus of FIG. 3.

FIG. 4 shows a block diagram of one of digital waveform generators 54 of apparatus 22 (FIG. 3). It should be understood that each of digital waveform generators 54 are equivalent, with the exception being the particular resultant signal that they produce. Accordingly, the following discussion pertains to each of digital waveform generators 54 of apparatus 22.

Digital waveform generator includes a divide-by-N counter 80 and a divide-by-M counter 82. Each of counters 80 and 82 is configured to receive first reference signal 76. Divide-by-M counter 82 is further configured to receive second reference signal 78. First reference signal 76 received by divide-by-M counter 82 serves as a synchronization signal to synchronize the operation of divide-by-M counter 82 with divide-by-N counter 80.

Divide-by-N counter 80 is a first frequency divider that divides an input frequency, i.e., 15 MHz first reference signal 76 by a value "N". The output signal, i.e., a first resultant signal portion 84, of divide-by-N counter 80 is a one clock-cycle wide square wave, which occurs at a rate equal to the 15 MHz first reference signal 76 divided by N. Similarly, divide-by-M counter 82 is a second frequency divider that divides an input frequency, i.e., 3 kHz second reference signal 78 by a value "M". The output signal, i.e., a second resultant signal portion 86, of divide-by-M counter 82 is a one clock-cycle wide square wave, which occurs at a rate equal to the 3 kHz second reference signal 78 divided by M.

A logic gate 88 is in electrical communication with an output of each of divide-by-N and divide-by-M counters 80 and 82, respectively. Logic gate 88 has a first gate input 90 for receiving first resultant signal portion 84 and a second gate input 92 for receiving second resultant signal portion 86. In addition, logic gate 88 has a gate output 94 for producing a resultant signal 96.

In a preferred embodiment, logic gate 88 is an AND gate. An AND gate simulates the function of the logical operator AND. As such, AND gate 88 emits resultant signal 96 only when first and second resultant signal portions 84 and 86, respectively, are coincident, i.e., only when portions 84 and 86 are "high". Furthermore, since divide-by-M counter 82 is synchronized with divide-by-N counter 80, resultant signal 96 is a square wave signal with sharp rising and falling edges. Each resultant signal 96 from each of digital waveform generators 54 is subsequently combined at combiner 56 (FIG. 3) to produce therapeutic signal 31 at first electrode 26.

FIG. 5 shows an exemplary table 98 of frequencies used to produce resultant signals 96 that are combined to form therapeutic signal 31 (FIG. 3). In an exemplary embodiment, apparatus 22 includes twelve digital waveform generators 54. The twelve digital waveform generators 54 are distinguished as channels 100 and are labeled one through twelve in table 98.

Table 98 includes a first data set 102 that represents a value "N" 104 and a resulting first, or "high", frequency 106 of first resultant signal portion 84 (FIG. 4) produced by divide-by-N counter 80 (FIG. 4). Table 98 further includes a second data set 108 that represents a value "M" 110 and a resulting second, or "low", frequency 112 of second resultant signal portion 86 (FIG. 4) produced by divide-by-M counter 82. By way of example, a first waveform generator 54, having channel 100 of "1", produces first resultant signal portion 84 exhibiting first frequency 106 of 3920 Hz and second resultant signal portion 86 of 11.9 Hz.

In a preferred embodiment, first frequency 106 falls within a first range of 2000 to 17,000 cycles per second, i.e., Hz, and second frequency 112 falls within a second range of 0.3 to 15 cycles per second, i.e., Hz. As such, each of digital waveform generators 54 produces second resultant signal portion 86 exhibiting second frequency 112 that is lower than first frequency 106 of first resultant signal portion 84.

Furthermore, value "N" 104 and value "M" 110 are advantageously selected such that resultant signals 96 from digital waveform generators 54 are harmonically non-related. Accordingly, the generated therapeutic signal 31 has a pseudorandom signal characteristic. It is believed that the pseudorandom signal characteristic of therapeutic signal 31 is most effective for stimulating human tissue, such as scalp 32 (FIG. 1).

Although twelve digital waveform generators 54 are available in apparatus 22 (FIG. 3), all need not be utilized. For example, one of waveform generators 54, having channel 100 of "5", is unused. In addition, other waveform generators 54 need not include both a high frequency component, i.e., first frequency 106, and a low frequency component, i.e., second frequency 112. Rather, only one of counters 80 and 82 may be employed. For example, waveform generators 54 represented by channels 100 labeled "2", "6", and "8" only generate resultant signal 96 that includes second resultant signal portion 86 exhibiting low frequency 112. In such a scenario, the FPGA configuration of digital waveform generator 54 is readily adapted by removing logic gate 88, such that resultant signal 96 is equivalent to second resultant signal portion 86.

The values "N" and "M" 104 and 110, respectively, to generate first and second frequencies 106 and 112 are employed in a preferred configuration of apparatus 22.

However, those skilled in the art will recognize that other values for N and M that yield harmonically non-related resultant signals 96 may be envisioned. Moreover, through the FPGA configuration of apparatus 22, other values for N and M may be readily programmed into apparatus 22.

Figure 6:
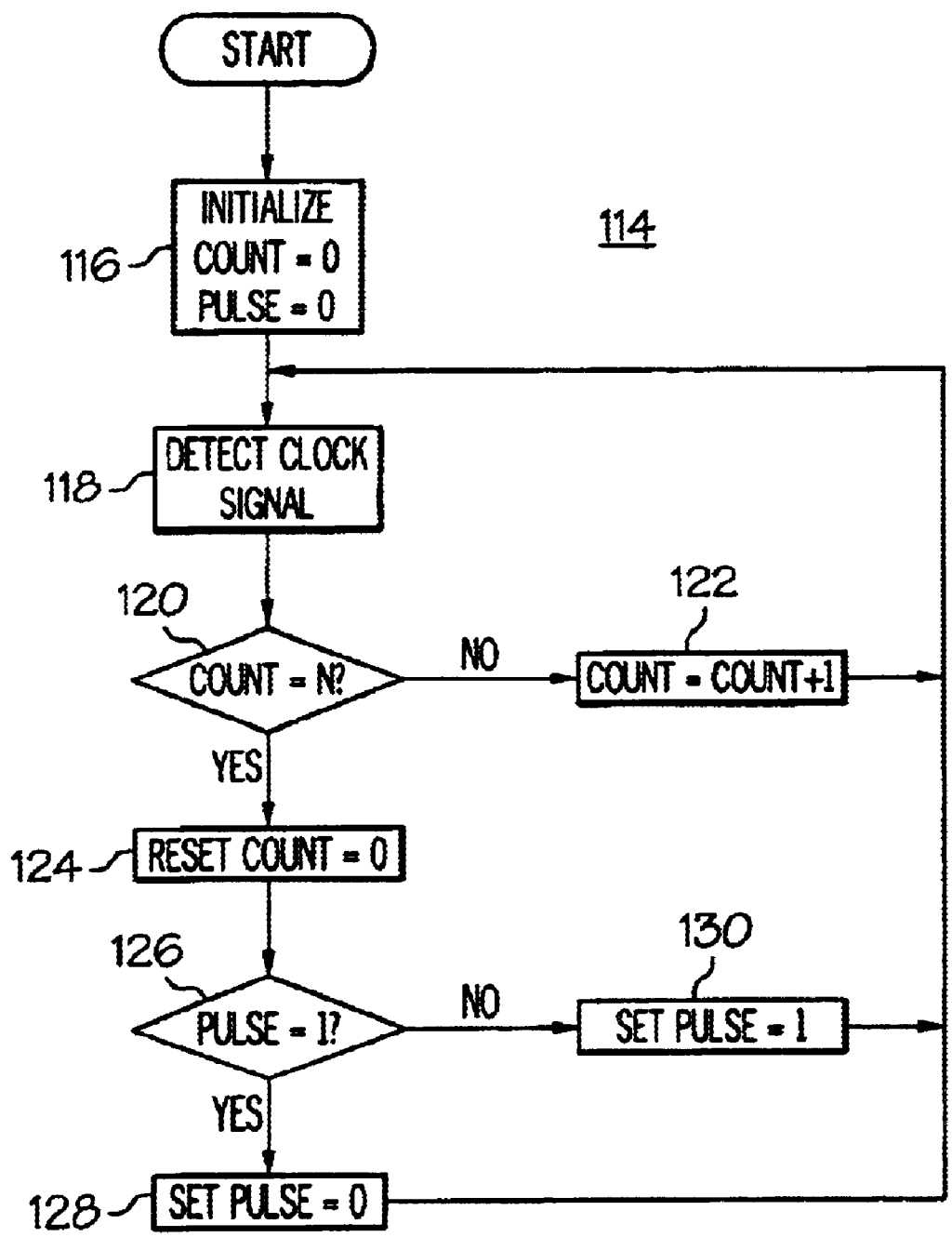
FIG. 6 shows a flow chart of a divide-by-N process performed by a divide-by-N counter of the digital waveform generator of FIG. 4.

FIG. 6 shows a flow chart of a divide-by-N process 114 performed by divide-by-N counter 80 (FIG. 4) of digital waveform generator (FIG. 4). Process 114 begins with a task 116. At task 116, divide-by-N counter 80 is initialized to zero. In addition, first resultant signal portion 84 is set low (i.e., PULSE=0). Next, as apparatus 22 is activated, a task 118 detects a pulse of the clock signal, i.e., first reference signal 76.

When first reference signal 76 is detected, a query task 120 determines whether the count of divide-by-N counter 80 is equal to value "N" 104 (FIG. 5). When count does not equal value "N" 104, process 114 proceeds to a task 122.

Task 122 increments the count value by one, i.e., COUNT=COUNT+1. Following task 122, process 114 loops back to task 118 to detect the next pulse of first reference signal 76.

At query task 118, when the count equals value "N" 104, process 114 proceeds to a task 124. At task 124, divide-by-N counter 80 is reset to zero. Following task 124, a query task 126 determines whether first resultant signal portion 84 is currently high, i.e., PULSE=1. When first resultant signal portion 84 is currently high, program flow proceeds to a task 128 where first resultant signal portion 84 is switched to low, i.e., PULSE is set to 0. However, when query task 126 determines that first resultant signal portion 84 is currently low, i.e. PULSE=0, program flow proceeds to a task 130 where first resultant signal portion 84 is switched to high, i.e., PULSE is set to 1. Following either of tasks 128 and 130, program control loops back to task 118 to continue detecting pulses of first reference signal 76. Consequently, through the execution of the tasks of process 114, divide-by-N counter 80 effectively divides first reference signal 76 by value "N" 104 to produce first resultant signal portion 84.

Figure 7:
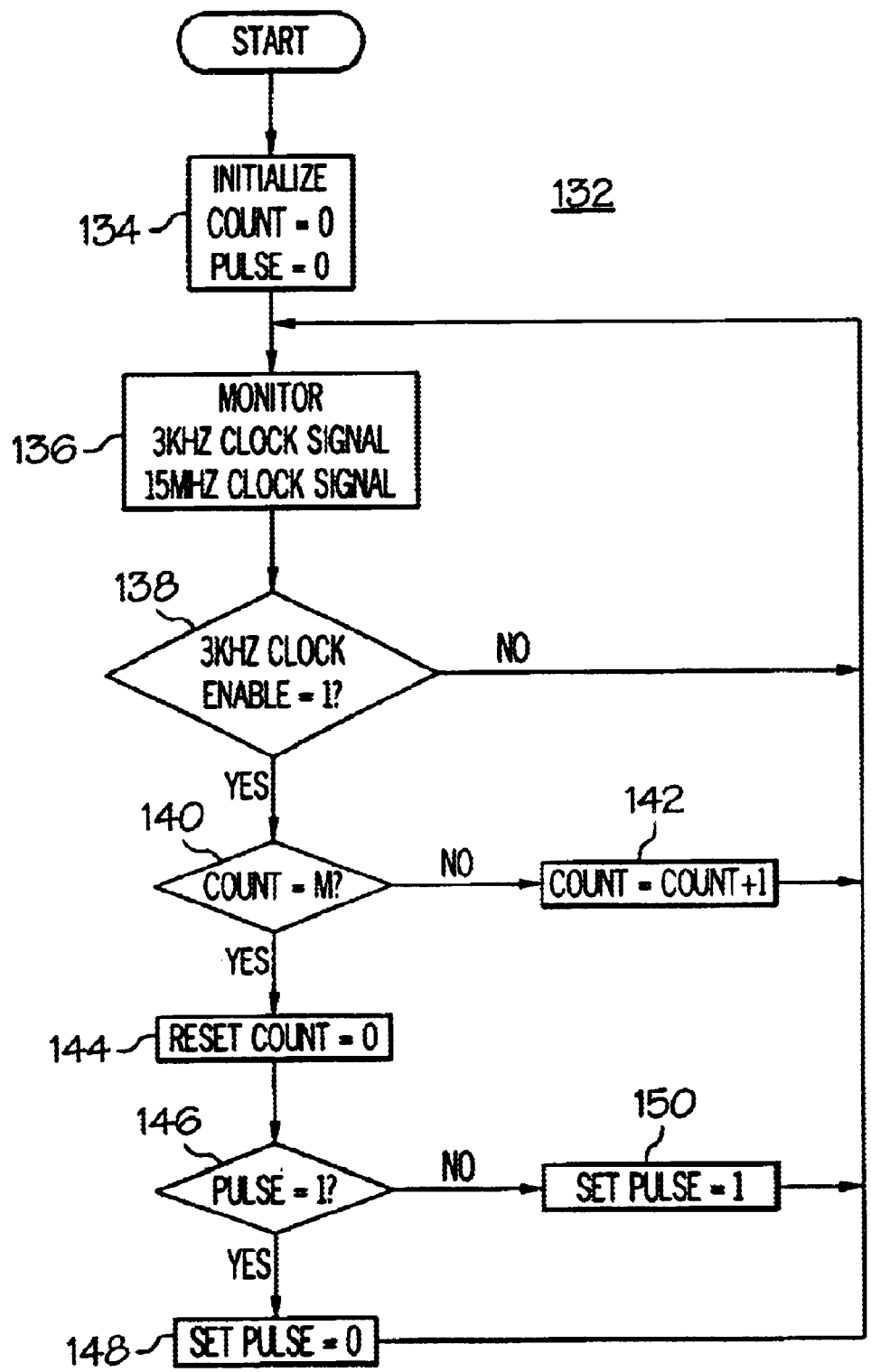
FIG. 7 shows a flow chart of a divide-by-M process performed by a divide-by-M counter of the digital waveform generator of FIG. 4.

FIG. 7 shows a flow chart of a divide-by-M process 132 performed by divide-by-M counter 82 (FIG. 4) of digital waveform generator (FIG. 4). Process 132 begins with a task 134. At task 134, divide-by-M counter 82 is initialized to zero (i.e., COUNT=0) and second resultant signal portion 86 is set low (i.e., PULSE=0). Next, as apparatus 22 is activated, a task 13 monitors first reference signal 76 (15 MHz clock signal) and second reference signal 78 (3 kHz clock signal).

In response to task 136, a query task 138 determines whether a pulse of second reference signal 78 is detected, i.e., 3 kHz clock enable=1. When second reference signal 78 is not detected, program control loops back to task 136 to continue monitoring for the rising edge of second reference signal 78. However, when second reference signal 78 is detected, process 132 proceeds with a query task 140.

Query task 140 determines whether the count of divide-by-M counter 82 is equal to value "M" 110 (FIG. 5). When count does not equal value "M" 110, process 132 proceeds to a task 142.

Task 142 increments the count value by one, i.e., COUNT=COUNT+1. Following task 142, process 132 loops back to task 136 to continue monitoring first and second reference signals 76 and 78, respectively.

At query task 140, when the count equals value "M" 110, process 132 proceeds to a task 144. At task 144, divide-by-M counter 82 is reset to zero. Following task 144, a query task 146 determines whether second resultant signal portion 86 is currently high, i.e., PULSE=1. When second resultant signal portion 86 is currently high, program flow proceeds to a task 148 where second resultant signal portion 86 is switched to low, i.e., PULSE is set to 0. However, when query task 146 determines that second resultant signal portion 86 is currently low, i.e. PULSE=0, program flow proceeds to a task 150 where second resultant signal portion 86 is switched to high, i.e., PULSE is set to 1. Following either of tasks 148 and 150, program control loops back to task 136 to continue detecting pulses of first and second reference signals 76 and 78. Consequently, through the execution of the tasks of process 132, divide-by-M counter 82 effectively divides second reference signal 78 by value "M" 110 to produce second resultant signal portion 86 which is synchronized with first resultant signal portion 84.

Referring back to FIG. 1, a treatment utilizing apparatus 22 involves massage of scalp 32 by use of first electrode 26 over the head, forehead area frontalis muscle, neck area and shoulder area for relaxation and stimulation. Massage may be performed with subject 20 in an upright position and/or lying on a right side, left side, or on his or her back. While massaging with first electrode 26, subject grips second electrode 30. The operator "works" the layers of scalp, i.e., galea 40 and connective tissue 42. Recall that several skin layers overly connective tissue 42. These layers, i.e., epidermis 34, dermis 36, and adipose tissue layer 38 loosen far easier than connective tissue 42. The operator may apply moderate forward pressure and back off of that forward pressure repetitively in a kneading action without moving first electrode 26 off scalp 32 until the operator senses that the connective tissue has loosened. Although described in connection with scalp 32, those skilled in the art will recognize that the technique is applicable to other body portions as well.

In summary, the present invention teaches of an improved apparatus for generating a therapeutic signal for the electrical stimulation of human tissue. The apparatus is configured utilizing an FPGA technique so that the therapeutic signal may be readily modified. Moreover, the digital waveform generators of the apparatus generate square waves with fast rise and fall times, which are believed to improve the efficacy of the treatment. In addition, the apparatus of the present invention provides the operator with greater awareness of tight and loose areas of the scalp, so as to focus and enhance the effectiveness of the treatment.

Although the preferred embodiments of the invention have been illustrated and described in detail, it will be readily apparent to those skilled in the art that various modifications may be made therein without departing from the spirit of the invention or from the scope of the appended claims.

What is claimed is:

1. An apparatus for the electrical stimulation of human tissue, said apparatus comprising:

a signal generator for providing a reference signal at a reference frequency;

a plurality of digital waveform generators in communication with said signal generator for producing different harmonically non-related resultant signals, each of said digital waveform generators including a frequency divider for dividing said reference frequency of said reference signal to produce one of said resultant signals;

a combiner in communication with an output of each of said plurality of digital waveform generators, said combiner combining said resultant signals from said each of said digital waveform generators to produce a therapeutic signal having a pseudorandom signal characteristic;

a first electrode in communication with said combiner;

a second electrode maintained at a ground potential from which said therapeutic signal from said first electrode is referred, said therapeutic signal having an electrical potential sufficient to stimulate said human tissue.

2. An apparatus as claimed in claim 1 wherein said resultant signals are square wave signals.

3. An apparatus as claimed in claim 1 wherein said frequency divider is a first frequency divider, said first frequency divider produces a first resultant signal portion of said one of said reference signals, and said each of said digital waveform generators further includes:

a second frequency divider for receiving a second reference signal at a second reference frequency and dividing said second reference signal to produce a second resultant signal portion; and a logic gate having a first gate input for receiving said first resultant signal portion and a second gate input for receiving said second resultant signal portion, and a gate output for producing said one of said resultant signals in response to said first and second resultant signal portions.

4. An apparatus as claimed in claim 3 wherein said second frequency divider is in communication with said signal generator for receiving said reference signal, said reference signal being employed to synchronize said second resultant signal portion with said first resultant signal portion.

5. An apparatus as claimed in claim 3 wherein:

said first resultant signal portion exhibits a first frequency; and said second resultant signal portion exhibits a second frequency, said second frequency being lower than said first frequency.

6. An apparatus as claimed in claim 5 wherein:

said first frequency is in a first range of 2000 to 17,000 cycles per second; and said second frequency is in a second range of 0.3 to 15 cycles per second.

7. An apparatus as claimed in claim 3 further comprising a third frequency divider having a divider input in communication with said signal generator, and having a divider output in communication with said second frequency divider, said third frequency divider generating said second reference signal at said second reference frequency.

8. An apparatus as claimed in claim 3 wherein said logic gate is an AND gate.

9. An apparatus as claimed in claim 1 wherein said human tissue is connective tissue underlying the skin surface of a designated body portion of a subject, said first electrode is pressed against said skin surface over said designated body portion, said second electrode is positioned to contact said skin surface at a location remote from said designated body portion, and said therapeutic signal is configured to pass from said one of said first and second electrodes to the other of said first and second electrodes in a path that extends through said connective tissue of said designated body portion.

10. An apparatus for electrically stimulating the organs associated with the human scalp, said apparatus comprising:

a signal generator for providing a reference signal at a reference frequency;

a plurality of digital waveform generators for producing different harmonically non-related resultant signals, each of said digital waveform generators including:

a first frequency divider in communication with said signal generator for dividing said reference frequency of said reference signal to produce a first resultant signal portion;

a second frequency divider for receiving a second reference signal at a second reference frequency and dividing said second reference signal to produce a second resultant signal portion; and a logic gate having a first gate input for receiving said first resultant signal portion and a second gate input for receiving said second resultant signal portion, and a gate output for producing one of said resultant signals in response to said first and second resultant signal portions;

a combiner in communication with an output of said each of said digital waveform generators, said combiner combining said resultant signals from said each of said digital waveform generators to produce a therapeutic signal having a pseudorandom signal characteristic;

a first electrode in communication with said combiner;

a second electrode maintained at a ground potential from which said therapeutic signal from said first electrode is referred, said therapeutic signal having an electrical potential sufficient to stimulate said organs associated with the human scalp.

11. An apparatus as claimed in claim 10 wherein said second frequency divider is in communication with said signal generator for receiving said reference signal, said reference signal being employed to synchronize said second resultant signal portion with said first resultant signal portion.

12. An apparatus as claimed in claim 10 wherein:

said first resultant signal portion exhibits a first frequency; and said second resultant signal portion exhibits a second frequency, said second frequency being lower than said first frequency.

13. An apparatus as claimed in claim 12 wherein:

said first frequency is in a first range of 2000 to 17,000 cycles per second; and said second frequency is in a second range of 0.3 to 15 cycles per second.

14. An apparatus as claimed in claim 10 further comprising a third frequency divider having a divider input in communication with said signal generator, and having a divider output in communication with said second frequency divider, said third frequency divider generating said second reference signal at said second reference frequency.

15. An apparatus as claimed in claim 10 wherein said logic gate is an AND gate.

16. An apparatus for the electrical stimulation of human tissue, said apparatus comprising:

a signal generator for providing a reference signal at a reference frequency;

a plurality of digital waveform generators in communication with said signal generator for producing different harmonically non-related resultant signals, each of said digital waveform generators including a frequency divider for dividing said reference frequency of said reference signal to produce one of said resultant signals, said one of said resultant signals being a square wave signal;

a combiner in communication with an output of each of said plurality of digital waveform generators, said combiner combining said resultant signals from said each of said digital waveform generators to produce a therapeutic signal having a pseudorandom signal characteristic;

a first electrode in communication with said combiner;

a second electrode maintained at a ground potential from which said therapeutic signal from said first electrode is referred, said therapeutic signal having an electrical potential sufficient to stimulate said human tissue.

17. An apparatus as claimed in claim 16 wherein said frequency divider is a first frequency divider, said first frequency divider produces a first resultant signal portion of said one of said reference signals, and said each of said digital waveform generators further includes:

a second frequency divider for receiving a second reference signal at a second reference frequency and dividing said second reference signal to produce a second resultant signal portion; and a logic gate having a first gate input for receiving said first resultant signal portion and a second gate input for receiving said second resultant signal portion, and a gate output for producing said one of said resultant signals in response to said first and second resultant signal portions.

18. An apparatus as claimed in claim 17 wherein said second frequency divider is in communication with said signal generator for receiving said reference signal, said reference signal being employed to synchronize said second resultant signal portion with said first resultant signal portion.

19. An apparatus as claimed in claim 18 wherein said human tissue is connective tissue underlying the skin surface of a designated body portion of a subject, said first electrode is pressed against said skin surface over said designated body portion, said second electrode is positioned to contact said skin surface at a location remote from said designated body portion, and said therapeutic signal is configured to pass from said one of said first and second electrodes to the other of said first and second electrodes in a path that extends through said connective tissue of said designated body portion.

* * * * *